United States Patent [19]
Van Dijk et al.

[11] Patent Number: 5,177,114
[45] Date of Patent: Jan. 5, 1993

[54] PROCESS FOR RECOVERING NATURAL GAS IN THE FORM OF A NORMALLY LIQUID CARBON CONTAINING COMPOUND

[75] Inventors: Christiaan P. Van Dijk, Houston; Lowell D. Fraley, Sugar Land, both of Tex.

[73] Assignee: Starchem Inc., Houston, Tex.

[21] Appl. No.: 861,351

[22] Filed: Mar. 30, 1992

Related U.S. Application Data

[63] Continuation of Ser. No. 508,928, Apr. 11, 1990, abandoned.

[51] Int. Cl.$^5$ .......................... C07C 7/06; C07C 1/04
[52] U.S. Cl. .................... 518/703; 518/706; 252/373; 585/314; 585/315
[58] Field of Search ............... 518/703, 706; 252/373; 585/314, 315

[56] References Cited

U.S. PATENT DOCUMENTS

| | | | |
|---|---|---|---|
| 2,482,284 | 9/1949 | Michael et al. | 518/703 |
| 3,866,411 | 2/1975 | Marion et al. | 258/373 |
| 3,894,102 | 7/1975 | Chang et al. | 518/713 |
| 4,011,275 | 3/1977 | Zahner | 518/713 |
| 4,121,912 | 10/1978 | Barber et al. | 258/373 |
| 4,346,179 | 8/1982 | Sugier et al. | 518/706 |
| 4,481,305 | 11/1984 | Jorn et al. | 518/705 |
| 4,522,894 | 6/1985 | Hwang et al. | 518/703 |

FOREIGN PATENT DOCUMENTS 3712008  10/1988  Fed. Rep. of Germany ...... 252/373

OTHER PUBLICATIONS

"Remote Natural Gas Considerations", by F. M. Floyd, A. E. Cover and J. L. Peterson.

*Primary Examiner*—Howard T. Mars
*Attorney, Agent, or Firm*—Pravel, Gambrell, Hewitt, Kimball & Krieger

[57] ABSTRACT

This invention comprises a method for converting natural gas to a normally liquid carbon containing compound, such as methanol and/or dimethyl ether and/or to gasoline grade liquid hydrocarbons and/or olefins. The method of this invention eliminates the need for steam reforming and/or adiabatic reforming with essentially pure oxygen of the natural gas to a synthesis gas. In accordance with the process of this invention, a synthesis gas may be produced at an operating pressure suitable for conversion thereof to methanol and/or dimethyl ether without the need for synthesis gas recompression. Further, the vent or bleed gas from the overheads after conversion to the crude product methanol/DME and/or its conversion to gasoline grade liquid hydrocarbons, generally has a BTU capacity required to serve as a fuel gas for supplying the energy needed for operation of a gas turbine which powers the gas compression equipment requirements by which the process of this invention may be practiced. Accordingly, the capital and operating cost associated with the production of methanol, DME and gasoline from natural gas is significantly reduced by the method of this invention and renders it economically feasible for natural gas recovery processing at remote locations.

6 Claims, 4 Drawing Sheets

PROCESS FOR RECOVERING NATURAL GAS IN THE FORM OF A NORMALLY LIQUID CARBON CONTAINING COMPOUND

This is a continuation of co-pending application Ser. No. 07/508,928 filed on Apr. 11, 1990 and now abandoned.

FIELD OF THE INVENTION

This invention comprises a process susceptible to economical practice for using natural gas, particularly remote location natural gas, either from gas wells or produced in association with crude, in the form of a normally liquid carbon containing compound which is suitable for fuel use or as a precursor to the production of olefins, methyl alkyl ethers, or synthetic gasoline.

BACKGROUND OF THE INVENTION

As an alternative source to gasoline refined from petroleum, methods for conversion of coal and/or methane to liquid phase fuels have been under consideration since the 1920's.

Such methods as have been devised for production of liquid phase fuels from non-liquid carbon containing materials, have to date been unable to compete economically with gasoline refined from petroleum. Such practice of synthetic gasoline production methods as has occurred to date (other than pilot plant studies) has been dictated by circumstances which override economic considerations.

In the 1930-40's, Germany produced liquid fuels from coal on a large scale. Such synthetic gasoline production was necessitated by Germany's lack of petroleum resources. Germany's synthetic production of gasoline from coal was accomplished by a processing technique known as the Fischer-Tropsch Synthesis (FTS). In FTS gasoline production, a carbon containing source material, typically coal or alternatively methane, is first converted to a gas stream containing carbon monoxide, carbon dioxide, hydrogen, water and impurities. The gas stream is then purified of water and adjusted in composition to a synthesis gas which is thereafter compressed to the operating pressures required for conversion to a hydrocarbon product stream by contact with an FTS catalyst. The resulting hydrocarbon stream is then sent to a separator wherein a liquid hydrocarbon stream is separated which is then fractionated to various hydrocarbon grades, including a gasoline grade hydrocarbon stream.

Since that time, the FTS process has been widely studied and various modifications have been devised to improve its economics for gasoline production. Nevertheless, it is still not feasible to synthetically produce gasoline by an FTS procedure which is cost competitive to petroleum refined gasoline and, absent factors which override economic concerns, it is not commercially practiced. To date, liquid fuel production by FTS is only practiced at those locations to which a reliable supply of refinery grade petroleum crude is unavailable. Today the Republic of South Africa, for instance, produces liquid hydrocarbons from coal/methane by an FTS procedure.

In the early 1970's as the prices of petroleum dramatically rose, researchers, particularly those at Mobil Oil Corporation, developed a class of molecular sieve catalysts which convert methanol and other methoxy containing compounds to olefins (MTO=methanol to olefins) and/or to gasoline grade hydrocarbons (MTG=methanol to gasoline). Methods for production of a methoxy containing starting material, such as methanol, from carbon source materials ranging from wood to coal to methane have long been known.

The destructive distillation of wood is the first process by which methanol was produced. In the mid 1920's, a synthetic method for producing methanol from hydrogen and carbon oxides was developed. This synthetic method was first practiced at high pressures (250–350 atmospheres). By the late 1960's, improvement in the catalyst used for methanol production permitted the more economical production of methanol from hydrogen and carbon oxides at a lower pressure of 50–100 atmospheres (~730–1470 psig).

The conventional wisdom prevailing relating to methanol production directs one to convert the carbon source material, whether naphtha or methane, to the required hydrogen and carbon oxides containing synthesis gas by steam reforming. Wherein a methanol plant is designed for operation on a petroleum residue feed stream or coal, to enable greater flexibility to handle feed streams of variable composition, conventional wisdom prevailing directs one to prepare the synthesis gas by partial oxidation of the carbonaceous material feed with essentially pure oxygen.

Though methods for production of methanol from a synthesis gas are known, the relatively low equilibrium conversion of hydrogen and carbon monoxide to methanol requires a large recycle of the unreacted hydrogen and carbon monoxide in order to obtain a high efficiency of conversion of carbon input into methanol product. This significantly increases the size of equipment, and therefore the capital cost of a coupled methane to methanol to gasoline operation. Fortunately, the Mobil methanol to gasoline conversion catalyst was also found to be operative to convert dimethyl ether (DME) to gasoline. Accordingly, one means for improving the economics for a methane to methanol to gasoline operation is to convert methane to a mixture of methanol and dimethyl ether to enhance the efficiency of the conversion of carbon input into methoxy carbon compounds which the Mobil catalyst can convert to gasoline. See for example U.S. Pat. No. 3,894,102.

With the development of Mobil's MTG process and the continuing escalation of crude oil prices, during the 1970-early 80's, it appeared that production of gasoline from methane at a cost competitive to refined gasoline could be accomplished by coupling a conventional methanol production plant front end to a Mobil MTG process as the finish end.

In the early 1980's New Zealand, which then depended for its gasoline supply totally on imported crude oil products, undertook at a cost of about 1.2 billion dollars to construct a plant for production of gasoline from methane. The overall plant design comprised two main units, one for the production of methanol from methane, and the second using the Mobil MTG technology for converting methanol to gasoline. In effect, the New Zealand synthetic gasoline plant is two separate plants built side-by-side on common grounds. The first plant is a standard methanol production plant to produce the methanol which is the raw feed required for the Mobil MTG plant. In the Mobil MTG plant, a portion of the methanol feed is converted to DME and this product stream is then converted to gasoline over a molecular sieve catalyst.

In the design of the New Zealand synthetic gasoline plant, the synthesis gas necessary for the production of methanol is prepared by steam reforming natural gas at a pressure of less than 20 atmospheres (~290 psig). The equipment required for steam reforming is both high in capital and operating costs. The synthesis gas is then compressed to a pressure of 100 atmospheres (~1470 psi), a procedure which requires high capital and operating cost compressing equipment, but which is necessary to the proper operation of a methanol conversion unit on such synthesis gas. In view of the then high and steady rise of crude oil prices experienced in the late '70's and early '80's, the high capital cost associated with steam reforming and compression of the synthesis gas to produce the methanol needed was not seen as a prohibitive economic disadvantage to installation of the synthetic gasoline plant.

Installation of the New Zealand plant was complete and operations commenced in 1985. At that time, crude oil prices had fallen significantly from the level they had earlier attained and synthetic gasoline produced by the New Zealand plant was, and still is, economically uncompetitive with the price of refined gasoline; in major reason because of the cost, both capital and operating, associated with producing methanol from methane.

The Mobil molecular sieve catalyst process for converting methanol and/or dimethyl ether (DME) to gasoline is attractive provided that methanol and/or dimethyl ether can be made available at a practical cost.

In an attempt to improve the economies of synthetic gasoline production using the Mobil MTG process Haldor Topsoe developed a process now commonly known as the Tigas process. The Tigas process integrates methanol synthesis and gasoline synthesis into a single process loop which eliminates the separation of methanol as a discrete intermediate product. To accomplish this integration, Tigas combines both strains of conventional wisdom prevailing in standard methanol production operations in order to eliminate the need to compress synthesis gas from a steam reformer to the pressure required for operation of a methanol plant. Accordingly, in the Tigas process, methane is first steam reformed in part at a pressure of about 30 to 50 atmospheres (440-730 psi) to a high $CO_2$ content precursor synthesis gas and the unreacted methane content of this precursor synthesis gas is then secondarily reformed by partial oxidation with essentially pure oxygen to produce a still $CO_2$ rich final synthesis gas having a pressure of about 28 to 48 atmospheres (410-700 psi). This final moderate pressure synthesis gas is then sent to a reactor containing a catalyst which is active for producing both methanol and dimethyl ether from the synthesis gas. Although this reactor operates at a somewhat lower pressure than does a methanol only reactor, because of its coproduction of dimethyl ether a high conversion of methane based carbon to combined methanol and dimethyl ether is still obtained. Total conversion of natural gas input carbon to a methoxy compound containing feed stream composition upon which the Mobil MTG process can operate is high. The methanol and dimethyl ether containing product gas stream is then reacted over a Mobil catalyst to convert the methoxy compounds thereof to liquid hydrocarbon compounds which are separated from the product gas stream and a portion of the residual overhead gasses containing unreacted hydrogen, carbon dioxide, methanol, ethane and olefins are recycled back to the inlet of the methanol/dimethyl ether reactor.

Although the Tigas design somewhat improves the economics for synthetic gasoline production from methane, it still requires a high capital cost steam reforming unit to which Tigas adds a requirement for a high capital cost oxygen plant to permit secondary reforming. The high capital cost required for a synthesis gas compressor is eliminated by Tigas in favor of a high capital cost oxygen plant to obtain in the tradeoff, a net reduction of capital and operating cost, after the obtainment of the synthesis gas, in the form of units of smaller duty size down stream. Though an improvement, the Tigas process is not economically feasible for synthetic gasoline production from methane in light of its high attendant capital cost.

Some variations to the basic Tigas process have been reported to further reduce the need for high capital cost items. One such variation is reported in U.S. Pat. No. 4,481,305. In this variation, an improvement in the economies of recycle is reported to be obtained compared to the standard recycle procedure described by U.S. Pat. No. 3,894,102 to be used with the Mobil MTG process. The improvement requires that adjustments be made to the composition of the synthesis gas feed to a methanol/dimethyl ether production reactor such that the synthesis gas feed will contain carbon monoxide and hydrogen in a $CO/H_2$ ratio of above 1 and contain carbon monoxide and carbon dioxide in a $CO/CO_2$ ratio of from 5 to 20. A synthesis gas of such composition may be obtainable from coal or a similar carbonaceous starting material. It is, however, not economically feasible to prepare a synthesis gas of such composition from methane.

Even though synthetic gasoline production processes such as FTS, standard Mobil and/or Tigas have undergone steady improvements intended to render them more economical to the production of synthetic gasoline from methane, they are today still unable to produce gasoline at a cost competitive to that refined from petroleum crude. This is so, even where a source of low cost methane is conveniently located to or transportable to the synthetic gasoline production plant site.

Natural gas resources are located in many areas which are remote from means for transporting such natural gas conveniently and/or economically to markets. In many such remote locations, the natural gas is produced in association with crude oil production and the so-produced natural gas must be disposed of, by flaring or reinjection, in order to produce the crude. Flaring has become an unacceptable method of disposal since it is an economic waste of a diminishing hydrocarbon resource and is also a source of air pollution. Reinjection, which adds to the cost of crude oil production, is often unacceptable both in view of its cost and the adverse effects it may impose upon crude oil production from the field itself.

The inability to dispose of natural gas produced in association with crude at a remote location in a manner which is economically, governmentally and environmentally acceptable has brought crude oil production at some locations to a halt. Application of a currently existing process for conversion of such remotely located natural gas to methanol and/or for synthetic gasoline production from such remotely located natural gas is not economically feasible in view of the great capital cost associated with the equipment necessary to practice such processes.

A process for converting natural gas to methanol, dimethyl ether or gasoline which is feasible for practice from the standpoint of the capital and operating cost associated thereto is a highly desired goal.

SUMMARY OF THE INVENTION

This invention comprises a method for converting natural gas to a normally liquid carbon containing compound, such as methanol and/or dimethyl ether and/or to gasoline grade liquid hydrocarbons and/or olefins. The method of this invention eliminates the need for steam reforming and/or adiabatic reforming with essentially pure oxygen of the natural gas to a synthesis gas. In accordance with the process of this invention, a synthesis gas may be produced at an operating pressure suitable for conversion thereof to methanol and/or dimethyl ether without the need for synthesis gas recompression. Further, the vent or bleed gas from the overheads after conversion to the crude product methanol/DME and/or its conversion to gasoline grade liquid hydrocarbons, generally has a BTU capacity required to serve as a fuel gas for supplying the energy needed for operation of the gas compression equipment requirements by which the process of this invention may be practiced. Accordingly, the capital and operating cost associated with the production of methanol, DME and gasoline from natural gas is significantly reduced by the method of this invention and renders it economically feasible for natural gas recovery processing at remote locations.

The process of this invention comprises the steps of reacting a natural gas with a quantity of an oxygen containing gas mixture containing at least 50 mole percent nitrogen such that, upon the completion of the reaction, a reformed gas is produced having a temperature between 1800° and 2500° F. and at least about 90 mole percent of the natural gas hydrocarbon carbon components are converted to carbon monoxide and carbon dioxide and about 1 to about 10 mole percent of such natural gas hydrocarbon carbon components are present in the reformed gas as methane; cooling such reformed gas stream to condense water; removing condensed water from said cooled reformed reformed gas stream to yield a synthesis gas stream; heating said synthesis gas stream to a temperature of from about 435° to about 500° F. and passing said heated synthesis gas stream at a pressure of about 400 to about 2,000 psia into contact with a catalyst composition which promotes reaction between hydrogen and carbon monoxide to produce a gas stream containing a quantity of a methoxy compound comprising methanol or dimethyl ether, and a gas balance comprising nitrogen, carbon monoxide, hydrogen, carbon dioxide, water and residual natural gas components. In one embodiment of the process, the resulting gas stream may be cooled to condense and separate therefrom a substantial quantity of the methoxy compound content thereof and the gas stream balance reheated to a temperature of from about 435° to about 500° F. and then passed at a pressure of from about 350 to about 1950 psia into a second contact with a catalyst composition which promotes the reaction between hydrogen and carbon monoxide to a second quantity of methoxy compounds. It is preferred that such gas stream is again contacted with such catalysts, in a plug flow mode, by passing said gas stream balance into a second reactor vessel containing such catalyst to produce a second product gas stream. Wherein a plug flow mode of second contact is utilized, it is preferred to cool the second product gas stream to condense and remove therefrom a substantial quantity of the methoxy compound content thereof.

Such second contact of the gas stream balance with a catalyst for conversion to a methoxy compound may also be accomplished by recycle of the gas stream balance into combined admixture with said synthesis gas stream.

The presence of a substantial mole percent of inert $N_2$ in the oxygen containing gas mixture with which the natural gas is reacted to form the synthesis gas composition has, surprisingly, been found not to greatly affect a need to increase the pressure required to convert the carbon monoxide and hydrogen components therein to methoxy compounds, particularly methanol and DME compounds, by contact with catalysts compositions typically employed to affect such conversion with a synthesis gas having a low $N_2$ content as prepared by steam reforming, adiabatic reforming with essentially pure oxygen, or a combination thereof. When making only methanol, the absence of need to greatly increase the pressure follows from the decision to accept lower conversions. Surprisingly, the admittedly negative effect of this lower conversion combined with the low cost of remotely located natural gas, is more than outweighed by the lower capital cost resulting from the use of a high nitrogen content oxygen containing gas to form the synthesis gas which eliminates the need to prepare the synthesis gas by primary reforming with steam or with essentially pure oxygen. Also, the high nitrogen content of the synthesis gas allows plug flow conversion to methanol in two or three reactors in series, thus eliminating the costly recycle.

For the case of combined methanol-DME manufacture the preferred pressure range is similar to that of the standard methanol process, notwithstanding the large $N_2$ content. This is especially the case when first methanol is prepared and separated in one or two steps before contact of the remaining synthesis gas with a methanol-DME catalyst to prepare a methanol-DME mixture. The advantage of being able to use plug flow reactors also applies in this case and is important.

Accordingly, this discovery permits production of methanol and/or DME from natural gas using standard methanol/DME catalyst compositions and conversion technology but without the need for employing a high capital cost steam reformer or a high capital cost oxygen plant as are required in methanol conversion units of conventional design, and this without greatly increasing the capital cost of the rest of the process facility.

As noted, methanol solely can be produced and recovered as a crude product for use as such as fuel, as feed to a methyl tertiary butyl—or methyl tertiary amyl ether plant, or as a feed for conversion to olefins, gasoline or other desirable products by contact with a Mobil catalyst. Alternatively, if plug flow multiple methanol and methanol/DME conversions are used, a first portion of the synthesis gas can be converted to crude methanol which is separately recovered, and the unreacted carbon monoxide and hydrogen content of such gas subsequently contacted with a catalyst for conversion to methanol/DME with the product gas resulting from the subsequent contact utilized as the feed gas composition for conversion over a Mobil catalyst to olefins and gasoline grade liquid hydrocarbons. This opens an easy avenue to more complicated schemes as for instance advocated in U.S. Pat. No. 4,654,453, the disclosure of which is hereby incorporated by reference.

In yet other embodiments in which the process of this invention may be practiced, the need to compress the synthesis gas to a pressure necessary for conversion to methanol with standard methanol catalysts may be significantly reduced or even totally eliminated. This significantly reduces or eliminates the capital equipment costs associated to the need in standard methanol production methods for compressing the synthesis gas prepared by steam reforming or adiabatic reforming with essentially pure oxygen to the pressure needed for conversion to methanol.

Whether the process of this invention is utilized solely for crude methanol production, or whether it is used in combination with a Mobil MTG unit for production of gasoline, the final overhead gas from the finish end of this process contains a sufficient BTU content to be utilized to supply most, all or in excess of the fuel gas energy required for compression and heat exchanger equipment operation needed in the practice of this process. At times the BTU content of this final overhead gas may exceed all of the compression and heat exchange requirements for the process and excess power can be produced for export from the process, for instance in the form of electricity. In that case, other excess heat in the process can be used to generate steam and thus provide more power for electricity generation.

In a most preferred embodiment of the process, the finish end is an MTG unit the final vent or bleed gas from which is recycled as fuel to the expander drive side of a gas turbine, wherein by complete combustion with compressed air, the driving energy requirement is supplied for a first step of compression of the oxygen containing gas mixture used in this process and also for the operation of the gas compressors by which the natural gas stream and the oxygen containing gas mixture are compressed to the final pressures desired for the reaction therebetween which provides the carbon monoxide and hydrogen containing synthesis gas. As an alternative, the bleed gas stream may be utilized to generate low pressure steam for steam driven gas compressors.

In comparison to conventional methods for methanol production from a synthesis gas made by steam reforming or essentially pure oxygen reformed natural gas wherein the total conversion efficiency is about 80-90%, total conversion efficiency of carbon to crude methanol and/or DME in the process of this invention is about 60% when methanol only is produced and is from about 65-75% when methanol and DME are produced. However, such conversion levels are accomplished at such a dramatically reduced capital cost that the process of this invention is economically viable for application to remotely sourced natural gas for conversion thereof to normally liquid carbon containing compounds which are capable of competitive pricing to similar liquid carbon containing compounds produced by other methods or by refining from petroleum crude.

BRIEF DESCRIPTION OF THE DRAWINGS

In the different figures like parts are identically numbered.

DETAILED DESCRIPTION OF THE PREFERRED EMBODIMENTS

Figure 1:
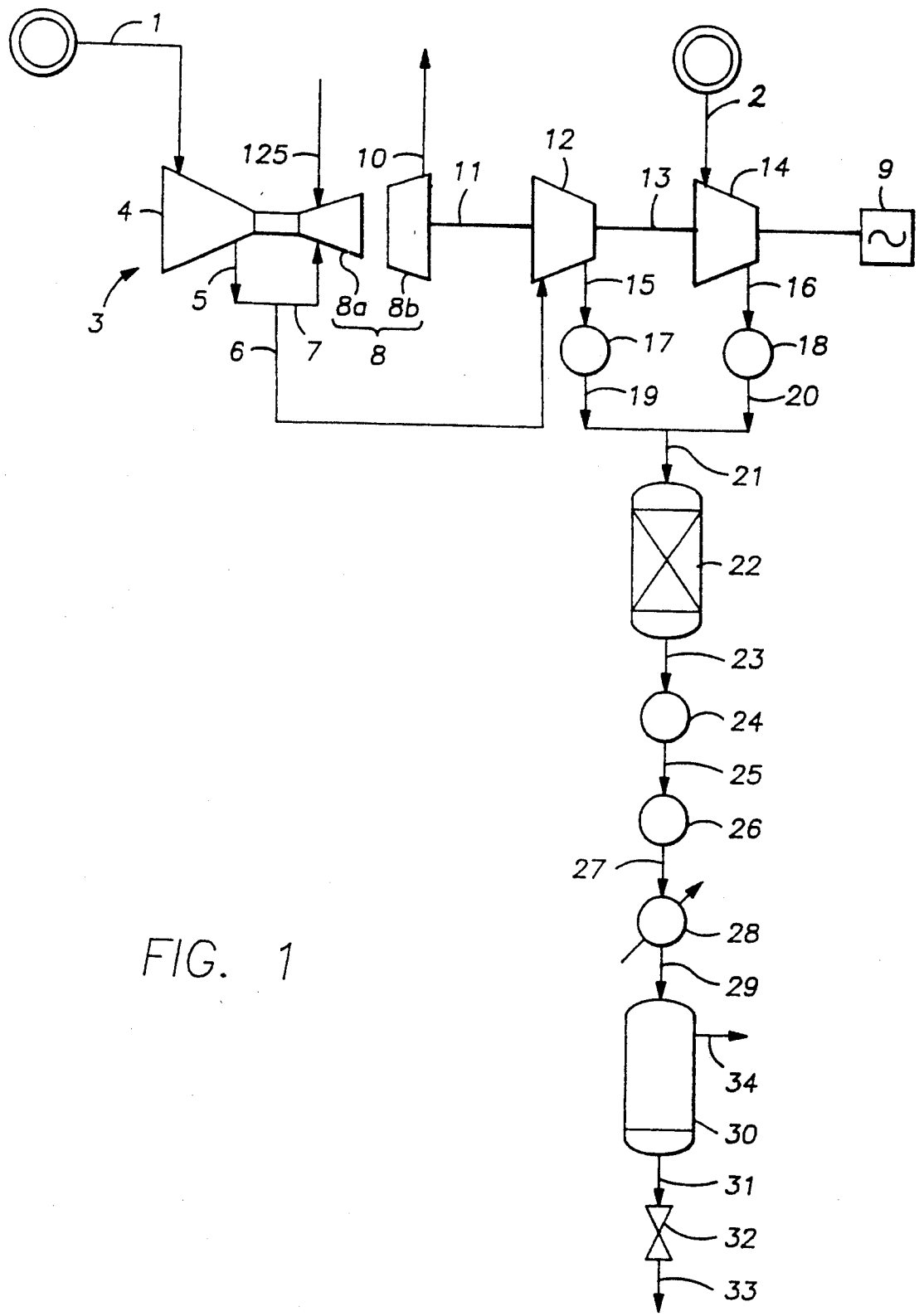
FIG. 1 schematically illustrates a unit design for synthesis gas production wherein a gas turbine fueled with the bleed gas from the finish end of the process is utilized to provide for the compression of the natural gas and air streams and to further provide the driving energy needed to operate other equipment requirements for the process. As illustrated, since the bleed gas 125 used as the fuel gas for the gas turbine 3 has a high $N_2$ content, it is possible to divert a portion of the compressed air 5 from the gas turbine compressor 4 as a compressed air feed 6 into air compressor 12 without violating the thermal and mass balance constraints to which the gas turbine was designed to operate.
Figure 2:
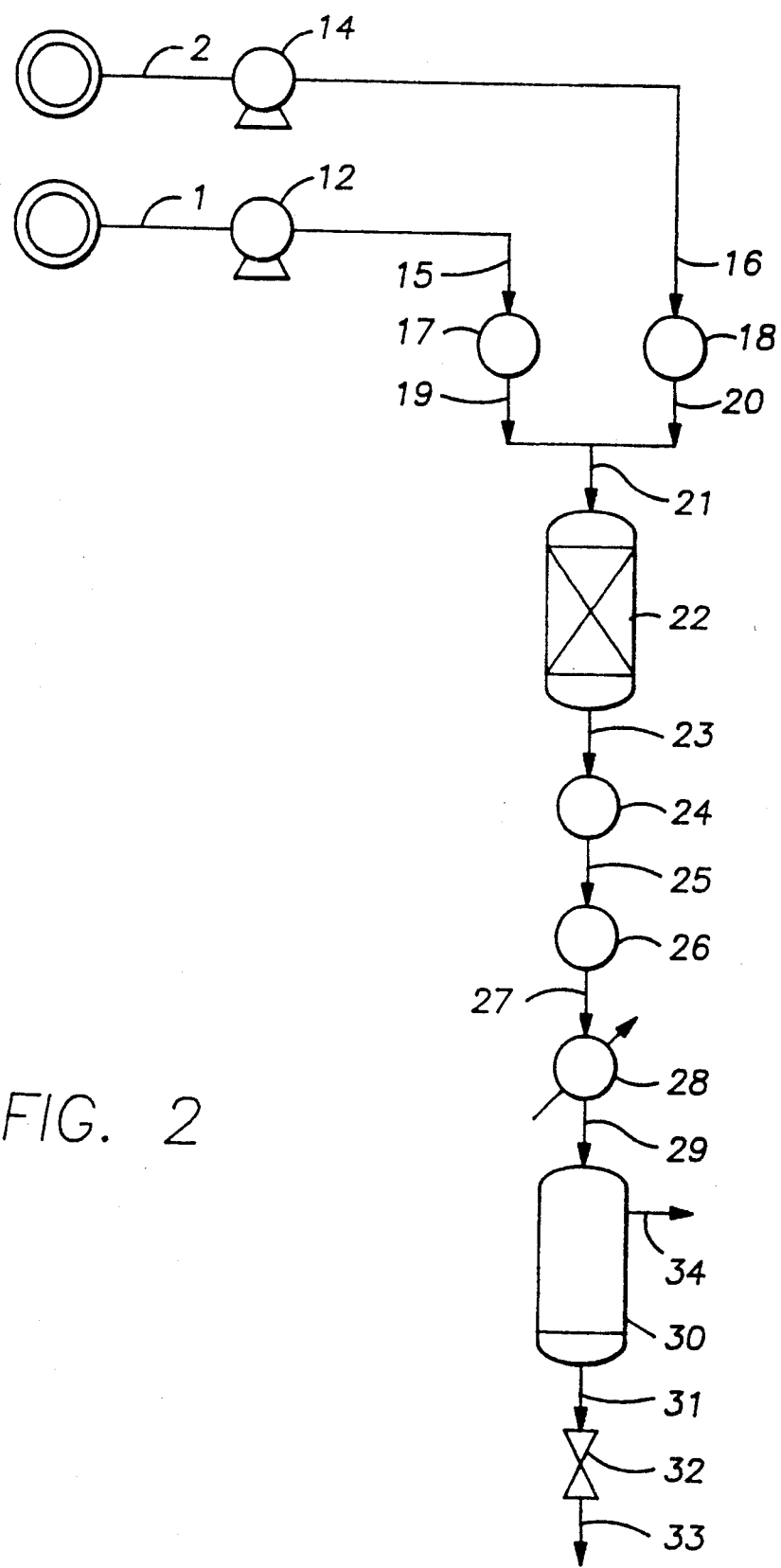
FIG. 2 schematically illustrates another embodiment of a unit within which a synthesis gas 34 may be prepared in accordance with the practice of this invention. The compressors 14 and 12 for compression of natural gas and air may be steam, electrically or turbine powered compressors.
Figure 3:
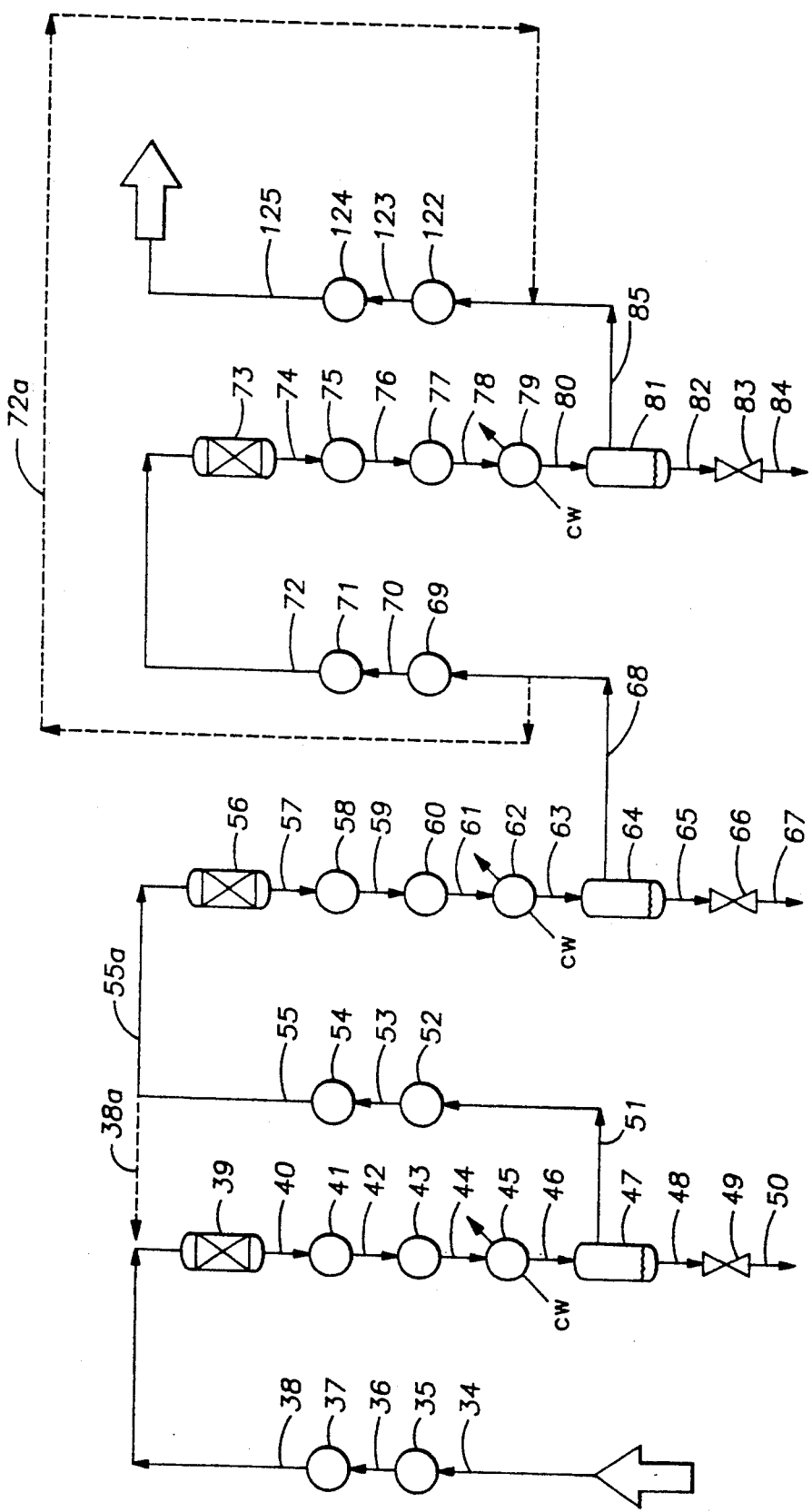
FIG. 3 schematically illustrates a unit design wherein a synthesis gas 34 as produced by either of the units illustrated by FIGS. 1 or 2 may be processed into and recovered as crude methanol only. Illustrated is the preferred embodiment for plug flow only processing wherein recycle via line 38a is omitted and a third methanol reactor 73, with its associated heat exchangers and a separator 69-85, is incorporated into the processing train. Alternatively the unit may be of a two reactor design with recycle via line 38a of a portion of the first reacted gas back to the inlet of first reactor 39, a second methanol reactor 56 for a plugflow finish, and with line 72a as the bleed gas outlet line. In the two reactor with recycle embodiment the third reactor 73 and the items 69-85 associated therewith would be omitted.
Figure 4:
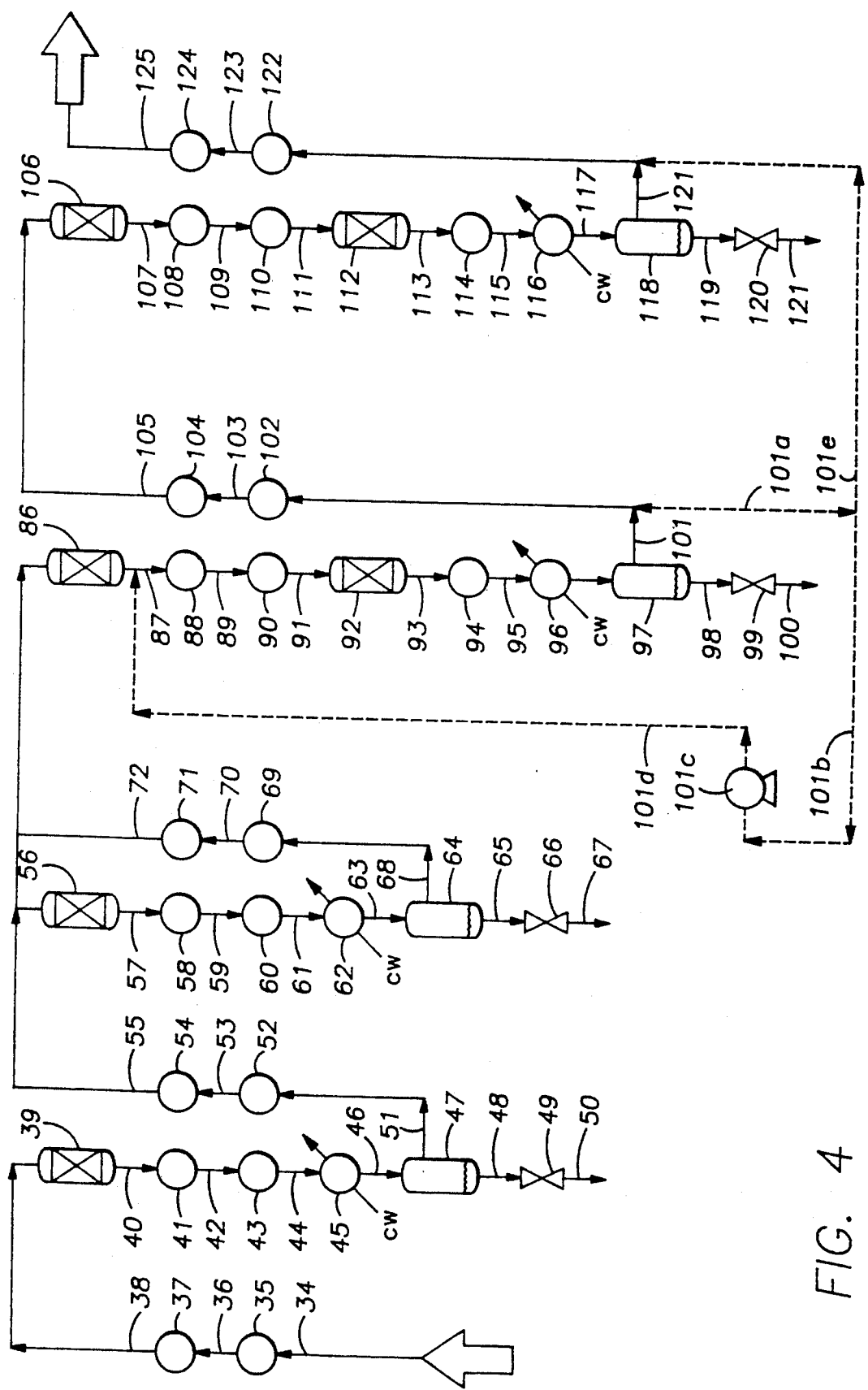
FIG. 4 schematically illustrates a unit design wherein a synthesis gas as produced by either of the units illustrated by FIGS. 1 or 2 may be processed in part to methanol which is recovered, and in part into normally liquid hydrocarbons of a gasoline grade. This unit is preferably of a plug flow only design. Phantom lining illustrates an alternative embodiment for a recycle mode of operation via lines 101a-101e in which embodiment process lines and reactors 102-121 may be omitted.

With reference to FIGS. 1 and 2, a natural gas stream 2, which has preferably been scrubbed of acid gas components (not illustrated) which has first been compressed to a desired level and then preheated by heat exchanger 18 is passed by line 20 into contact with an oxygen containing gas mixture containing at least 50 mole % nitrogen 1 which has first been compressed to the desired level and then preheated by heat exchanger 17 and passed therefrom by line 19. The so-compressed and preheated natural gas and oxygen containing gas mixture pass by line 21 into an adiabatic reactor 22 wherein they react to form a reformed gas from which water is condensed by cooling of the reformed gas. Lines 23, 25, 27 and 29 communicate the reformed gas from reactor 22 through heat exchangers 24, 26 and 28 and condensed water is separated from the cooled reformed gas in separator 30 and removed therefrom by line 31 under valve control 32 to line 33 for disposal or other use. The gas after water removal is a synthesis gas 34 which may be processed to methanol only, as illustrated by FIG. 3, or to a combination of methanol and gasoline each of which products are separately recovered, as illustrated by FIG. 4, or to gasoline only (last part of FIG. 4).

In the most preferred embodiments of the process of this invention the synthesis gas is produced at a pressure which is suitable for subsequent processing into a methoxy containing compound and/or gasoline without the need for further recompression of the synthesis gas. This reduces both the capital and operating cost associated with the compression of a gas which is of a high hydrogen content. The capital and operating cost associated with the compression of a natural gas and an oxygen containing gas, such as air, to a given pressure level is significantly less than that associated to the compression of a somewhat larger volume of synthesis gas containing a high level of hydrogen to a similar pressure.

Accordingly, in the most preferred embodiments of the process of this invention, a natural gas stream is first compressed to a pressure of from about 400 to about 2010 psia, preferably from about 400 to about 1530 psia, more preferably from about 600 to about 1200 psia, and thereafter the compressed natural gas stream is heated to a temperature of from about 800° to about 1400° F., more preferably from about 900° to about 1050° F. The oxygen containing gas stream is compressed to the same levels of pressure and the compressed oxygen containing gas stream is then heated to a temperature of from about 700° to about 1400° F., more preferably from about 800° to about 1050° F. The compressed and preheated natural gas and oxygen containing gas streams are then supplied to an adiabatic reactor vessel and reacted, in the presence or absence of an reforming catalyst, to produce a reformed gas stream having a pressure of from about 390 to about 1990 psia, more preferably from about 560 to about 1500 psia. After dewatering of the reformed gas, the resulting synthesis gas is, without need for further compression, at a pressure suitable to conversion to methanol only, or conversion to methanol in part for recovery and the remainder to methanol and/or DME, or wholly to methanol and DME as the feed for conversion over a Mobil catalyst to olefinic and gasoline grade normally liquid hydrocarbons.

In accordance with this process, natural gas is reacted with a quantity of an oxygen containing gas mixture having at least 50 mole % nitrogen to convert the hydrocarbon content of the natural gas to carbon monoxide, carbon dioxide, hydrogen and water wherein the molar ratio of hydrogen to carbon monoxide ($H_2/CO$) is between about 1.5 and about 1.9 and the molar ratio of carbon monoxide to carbon dioxide ($CO/CO_2$) is between about 10 and about 25. The reformed gas stream resulting from this reaction, on a water free basis, comprises from about 17 to about 50 mole % nitrogen, from about 27 to about 40 mole % hydrogen, from about 16 to about 27 mole % carbon monoxide, and the balance being carbon dioxide, and a residual unreacted hydrocarbon content of less than about 1.8 mole %.

The oxygen containing gas mixture utilized to produce such reformed gas may be air. The composition of dry air is about 21 mole % oxygen and 78 mole % nitrogen and a trace balance of other components. Such an oxygen containing gas mixture is adiabatically reacted with natural gas in the presence or absence of a reforming catalyst to produce a reformed gas of the above-described composition at a temperature of from about 1800° to about 2500° F. and a pressure of from about 400 to about 2000 psig. Preferably the adiabatic reaction of air with natural gas is accomplished by compressing the air to a pressure of from about 410 to about 2010 psig then heating the compressed air to a temperature of from about 700 to about 1400° F. and passing it into admixture with a natural gas stream which has first been compressed to the same pressure level and heated to a temperature of from about 800° to about 1050° F.

Wherein the so compressed and heated mixture of natural gas and air is adiabatically reacted in the absence of a catalyst, it is necessary that the natural gas and air mixture be formed so that the produced reformed gas has a final temperature of from about 2100° to about 2500° F. At such conditions, an adiabatic reaction between the hydrocarbon content of the natural gas, and the oxygen content of the air will occur in the absence of a catalyst to yield a reformed gas stream having the above mentioned final temperature and a pressure of from about 1 to about 10 psi lower than that of the unreacted inlet gas mixture. Wherein the adiabatic reaction is performed in the presence of a reforming catalyst, the natural gas and air mixture may be formed so that the produced reformed gas has an outlet temperature of from about 1900° to about 2100° F. and a pressure of from about 600 to about 2000 psig.

For the embodiment of this process which uses a reforming catalyst in the formation of a reformed gas, the catalyst composition may be any of the well known reforming catalysts, compositions as, for instance, described in *Petrochemical Handbook '89, Hydrocarbon Processing*, November 1989, page 106, which is incorporated herein by reference.

Alternatively, if desired, an oxygen enriched air may be utilized as the oxygen containing gas mixture for reaction with the natural gas. By "oxygen enriched air" it is meant a gas composition containing at least 50 mole percent nitrogen and an oxygen content greater than 21 mole %. Such oxygen enriched air may be obtained by dilution of a pure oxygen stream, if one is conveniently available, with air, or by passing atmospheric air through a relatively low cost, and accordingly inefficient, oxygen production unit.

The quantity of the oxygen for reaction with the natural gas must be selected such that on reaction, after contact with a reforming catalyst or with sufficient residence time at reaction temperature without a reforming catalyst, the reformed gas reaches the desired final temperature of between 1800° and 2500° F. On the basis of hydrocarbon carbon content of the natural gas, the CO and $CO_2$ content of the reformed gas is more than 80 mole %, preferably more than 90% CO. Between 1 and 10 mole % of the original hydrocarbon carbon atoms of the natural gas stream are present in the reformed gas as methane. The hydrogen to CO ratio in the reformed gas is between 1.5 and 1.9.

In most of the conditions proposed, it is preferred to employ a synthesis gas production unit of a design as illustrated in FIG. 1. This design utilizes a gas turbine 3 which is fueled by the final vent or bleed gas 125. The gas turbine provides both an initial stage of compression to the air stream and drives the gas compressors 12 and 14 by which the air and natural gas streams are compressed to the final level desired for adiabatic reaction to form the reformed gas stream. If desired, the bleed gas 125 can first be heated and expanded to about 3 psia above the expander inlet pressure, to provide a secondary amount of horse power.

A gas turbine 3 comprises a compressor unit 4 which is directly driven by an expander unit 8 which comprises a compressor drive expander 8a and a free turbine expander 8b. In the compressor drive expander 8a an oxidizable fuel gas is completely combusted with compressed air provided from compressor unit 4 which passes to the compressor drive expander 8b by lines 5 and 7. As the fuel gas is completely oxidized, it, together with the air, expands under heat in drive expander 8a. Therein the expanded gasses turn a turbine which by a drive shaft coupling to a turbine in compressor unit 4 drives the compressor unit turbine which compresses the inleted air 1. The combusted gas from drive expander 8a is passed to a free turbine expander 8b whereby further expansion of the combustion gasses turns a turbine therein. As illustrated, the free turbine drive shaft may be coupled to and drive gas compressors 12 and 14 and, insofar as horsepower is available from the free turbine draft shaft in excess of the compressor 12 and 14 duty requirements, it may be used to provide drive power to other equipment items, such as an electrical generator.

Gas turbines are designed by a criteria requiring a thermal and mass balance between the compressor unit 4 and the expander unit 8 which assumes air as the gas for compression. Under such design the entire volume of air compressed is required to be passed to the expander unit to limit its operating temperature to an upper operating temperature of from about 1800° to about 2000° F., the design limits for a gas turbine. The turbine design depends upon the passage of sufficient oxygen in the compressed air to the expander so that more than the stoichiometric content of oxygen is available to completely combust a hydrocarbon fuel source. The large amount of inert nitrogen and the excess oxygen act as coolants by which the maximum temperature of the expander unit 8 is maintained within operational limits.

Accordingly, it is not possible to divert a substantial portion of the compressed air out of the compressor side of a gas turbine without adequate compensation in feed to the expander side by adding a different stream, which has about equal coolant and mass balance effect as the quantity of diverted air. In general this is therefore not practiced.

In the design illustrated by FIG. 1 air at about atmospheric pressure 1 is introduced into the inlet of compressor unit 4 of gas turbine 3. Compressed air is emitted by line 5 from the compressor unit and a substantial portion of this compressed air—compressed to from about 6 to about 30 atmospheres (~90–450 psia), depending on the design of the gas turbine—is diverted by line 6 to the inlet of gas compressor 12 for further compression to the final pressure desired. The remaining portion of compressed air in line 5 is passed by line 7 into the air inlet of the expander drive unit 8a and bleed gas 125 is supplied as the fuel to the fuel inlet of the expander unit. Bleed gas 125 will contain from about 50 to about 85 mole % of $N_2$ and a total of from about 10 to about 30 mole % of CO, $H_2$, $CH_4$, olefins, hydrocarbons and/or methanol that provide the BTU energy necessary to power the expander. The high $N_2$ content of bleed stream 125 is sufficient to maintain the operation of the gas turbine in proper thermal and mass balance, thereby permitting a substantial portion of the compressed air in line 5 to be diverted from the gas turbine for use in the process.

Accordingly, in the unit design illustrated by FIG. 1, one may obtain in essence a first step of air compression at no net operating cost while also utilizing the gas turbine to provide the drive energy needed for other equipment operations.

Wherein the natural gas stream upon which this process is to operate is available at the process site at a pressure of from about 400 to about 1000 psig, it may readily be compressed to the required pressure for adiabatic reaction by steam or electrically driven compressors or by an independent gas turbine. If oxygen for air dilution is readily available, or, especially, if enriched air is provided, it may be preferred to employ a synthesis gas production unit of a design as illustrated in FIG. 2 wherein compressors 12 and 14 are driven by stream or electrical power generated by the complete oxidation of the final bleed gas from the finish end of the process. The reformed gas produced by the adiabatic reaction is cooled to a temperature of from about 100° to about 140° F. to condense and remove water therefrom. At a temperature of about 100° F., the final vapor pressure of water is about 0.95 psia, at a temperature of about 140° F. the final water vapor pressure is about 2.89 psia. Depending on the pressure, cooling to 140° F. will remove from the reformed gas most of the water produced in the reforming reaction.

The synthesis gas resulting after water removal is reheated to a temperature of from about 435° to about 500° F. and passed into contact with a catalyst composition which promotes reaction between hydrogen and carbon monoxide to produce methoxy compounds, particularly methanol and/or dimethyl ether or combinations thereof. Catalysts suitable for such reaction are well known. Examples of such catalysts compositions are described in U.S. Pat. No. 4,520,216, which discusses both the catalyst to make methanol only and catalyst mixtures for coproduction of methanol in admixture with DME. This patent is hereby incorporated by reference.

Preferably, the synthesis gas is contacted with such methoxy compound production catalysts at a pressure of from about 390 to about 1990 psig. Accordingly, wherein the methoxy catalyst composition is one for production of methanol only, it is preferred to initially produce the reformed gas under conditions wherein the resulting synthesis gas has a pressure of from about 700 to about 1990 psia. This manner of producing the synthesis gas eliminates the need to recompress it to the pressure required for the most efficient conversion of the synthesis gas to methanol by contact with the catalyst. Wherein the catalyst composition is one which promotes the co-production of methanol and dimethyl ether, the synthesis gas may be reacted at a pressure of from about 560 to about 1500 psia. At such lower pressures, the conversion of the synthesis gas carbon content to methanol and dimethyl ether is still efficient even though the pressure is significantly lower. Wherein the synthesis gas is initially produced to a pressure of from about 50 to about 700 psig, it is preferred to contact it with a methanol/DME catalysts since for such contact, the synthesis gas requires only a moderate degree of recompression before contact and, accordingly, both the size and cost of the required compressor for such operation is lower.

As noted, the end use intended for the synthesis gas stream determines the conditions most preferred for its initial production. One embodiment of the method of this invention contemplates the recovery of hydrocarbon content of a natural gas in the form of crude methanol only. Since methanol is a liquid, it may be conveniently stored and transported to an offsite location for subsequent processing, such as refining into market grade methanol, for use in manufacturing methyl ethers or for use as the feed stream to an offsite methanol to olefin or gasoline process. With reference to FIG. 3, wherein the process of this invention is designed for production of crude methanol only, synthesis gas 34 is passed by lines 34 and 36 through heat exchangers 35 and 37 whereby it is heated to the temperature required for the methanol reaction then passed by line 38 into reactor 39 and contacted with a methanol production catalyst. The first methanol product gas stream is passed by lines 40, 42 and 44 through heat exchangers 41, 43 and 45 and cooled to a temperature of from about 100° to about 140° F. to condense methanol and water from the gas stream. The so-cooled gas stream is passed by line 46 to separator 47 in which condensed methanol and water 50 are removed by line 48 under valve level control 49. The balance of the gas stream from separator 47 is passed by lines 51 and 53 through heat exchangers 52 and 54 and reheated to a temperature of from about 435° to about 500° F. and then passed by line 55 to reactor 56 and recontacted with a methanol production catalysts to further convert the unreacted hydrogen and carbon monoxide content thereof to a further quantity of methanol. This second contact with a methanol production catalyst may be accomplished in the form or a recycle of a portion of this reheated gas stream, balance by line 38a back to the inlet 38 of the first methanol reactor 39 where it is combined with fresh synthesis gas. More preferably, the second contact of this gas stream with a methanol production catalyst is accomplished in the mode of a plug flow reactor design, wherein this gas stream is passed by lines 55 and 55a as the input to a second catalyst vessel 56 containing a methanol production catalysts. When accomplished in a plug flow mode, it is preferred to cool the product gas resulting 57 to condense and remove therefrom the further quantity of methanol by passing it through heat exchangers and separator 58-67 as shown. The balance of the gas stream 68 from separator 64 is passed by line through heat exchangers 69 and 71 and is thereafter reheated to a temperature of from about 435° to about 500° F. and passed by line 72 to reactor 73 and again contacted it with a methanol production catalyst to still further convert the unreacted hydrogen and carbon monoxide content thereof to yet a further quantity of methanol. Again, this further contact may be accomplished in the form of a recycle of a portion of this gas stream to the inlet of the second methanol reactor (not illustrated). More preferably this further contact is accomplished as a plug flow of this gas stream to a third methanol reactor (as illustrated). However accomplished, the further quantity of methanol so produced is removed from the product gas stream by cooling it to a temperature of about 100° to about 140° F. and passing it to a separator and after methanol is removed the balance of the gas stream may be employed as a fuel gas to provide the energy requirements for compression of the natural and oxygen containing gas streams to the pressures desired for synthesis gas production. As illustrated in FIG. 3, wherein a gas turbine is used in the synthesis gas production unit (as illustrated by FIG. 1) it is preferred to heat the balance of gas stream (line 72a in the two reactor with recycle embodiment; line 85 in the three reactor plug flow embodiment) by passing it through heat exchangers 122 and 123 to heat it to a temperature of from about 400° to about 800° F. before passing it as the tail or bleed gas fuel 125 to the gas turbine. Such heating of the bleed gas fuel 125 maximizes the efficiency of the gas turbine.

Another preferred embodiment of this process is one intended for recovery of the hydrocarbon content of a natural gas in part as crude methanol and in part as gasoline grade liquid hydrocarbons. In this embodiment of the process, as illustrated by FIG. 4, the reformed gas is produced, as already described, to a pressure of from about 560 to about 1500 psig and a temperature of from about 1800° to about 2500° F. After cooling of the reformed gas to condense and remove water, the resulting synthesis gas 34 is reheated to a temperature of from about 435° to about 500° F. and passed at a pressure of from about 560 to about 1500 psig over a methoxy catalyst.

Two stages of methanol make and removal are preferred and are accomplished via lines, heat exchangers, methanol reactors and separators 39-67 as are shown in FIG. 4 and previously described with reference to FIG. 3. Following the second separation of methanol, the balance of the gas stream 68 from separator 64 is heated to a temperature of from about 435° to about 500° F. by passage through heat exchangers 69 and 71 and thereafter passed by line 72 to reactor 86 wherein the gas stream is contacted with a catalyst composition which promotes the coproduction of methanol and DME. The so reacted gas stream passes from reactor 86 by lines 87 and 89 through heat exchangers 88 and 90 and heated to a temperature of from about 600° to about 850° F. then passed by line 91 to reactor 92.

In reactor 92 the gas stream is contacted with a molecular sieve catalyst which promotes the reaction of methanol and DME to olefins first and then to gasoline boiling range components. Such catalyst compositions are known in the art, as described in U.S. Pat. Nos. 4,044,061; 4,058,576; and 4,058,576, the disclosures of which are hereby incorporated by reference. The design of reactor 92 may be of a fixed or fluidized catalyst bed mode of operation and can also be a combination of a heat exchanged reactor for the first reaction to olefins followed by a catalytic bed for the subsequent reaction to gasoline boiling range components as described in U.S. Pat. No. 4,058,576. Following reaction over the molecular sieve catalyst, the gas stream is passed from reactor 92 by lines 93 and 95 through heat exchangers 94 and 96 and cooled to a temperature of from about 100° to about 140° F. The so cooled gas stream is then passed to separator 97 wherein condensed hydrocarbons and olefins 100 are separated and removed by line 98 through level control valve 99.

In the most preferred embodiment of this process, the balance of the gas stream from separator 97 is reheated to a temperature of from about 435° to about 500° F. and again contacted a catalyst which promotes coproduction of methanol and DME in reactor 106. The product gas stream from reactor 106 is passed by lines 107 and 109 through heat exchangers 108 and 110 and heated to a temperature of from about 600° to about 850° F. then passed by line 111 into reactor 112 where it is contacted with a molecular sieve catalyst which promotes the reaction of methanol and DME to olefins and gasoline boiling range components. Following this reaction, the gas stream is passed by lines 113 and 115 through heat exchangers 114 and 116 and is cooled to a temperature of from about 100° to about 140° F. The so-cooled gas is passed by line 117 to separator 118 wherein condensed hydrocarbons and olefins 121 are separated and removed by line 119 through level control valve 120. The gas balance from separator 118 is passed by line 121 and 123 through heat exchangers 122 and 124 and is heated to a temperature of from about 400° to about 800° F., and thereafter passed by line 125 as the bleed gas fuel to the use of the synthesis gas production unit (as illustrated in FIGS. 1 and/or 2).

FIG. 4 also illustrates an alternate embodiment of the process wherein there is recycle of a portion of the gas balance from separator 97 via lines 101, 101a, and 101b to a compressor 101d which recompresses this portion of the gas balance to a pressure of from about 5 to about 10 psi above the pressure in the exit stream from the methanol-DME reactor 86, which pressure level allows balance of the gas stream in line 101d to be recombined with the exit gas stream from reactor 86. The other portion of the gas balance from separator 97 is passed by line 101e to heat exchangers 122 and 124 which prepares it as the bleed gas fuel 125 for service in the synthesis gas production unit. In this recycle mode embodiment of the process, the second methanol-DME and molecular sieve reactors 106 and 112, with their associated heat exchangers and product separator 102-121, are omitted.

Although the preferred embodiments of the process have been described with reference to the production of crude methanol only and with regard to methanol and gasoline, the process is not so limited. Other molecular sieve catalyst compositions, as described in U.S. Pat. No. 4,788,369 may be employed in place of a MTG catalyst for the production of other desirable compositions from methanol and/or DME, like for instance that proposed in U.S. Pat. No. 4,654,453 wherein excess isobutane produced in the MTG process is reacted with olefins made in the MTO process. This more complicated scheme has merit from the standpoint of octane improvement.

The invention is further illustrated but not limited by the examples which follow. In each of the following examples a feed rate in "moles per hour" (MPH) for a natural gas stream of the following composition is assumed, namely, a total feed of 102 MPH comprising in MPH, 91 methane, 5 ethane, 3 $CO_2$ and 3 $N_2$. Such a feed rate for a natural gas of such composition corresponds to treating about $10^6$ standard cubic feet per day (cfd) of natural gas. Production of a reformed gas by adiabatic reaction with air is assumed (using 21 mole % $O_2$ and 79 mole % $N_2$), with the gas turbine unit design of FIG. 1, wherein the final vent or bleed gas is utilized as the fuel gas for operation of the gas turbine. The gas turbine assumed is one which compresses inlet air from 1 atmosphere to 12 atmospheres absolute in the compressor unit of the gas turbine and has an efficiency of 7800 BTUs per brake housepower.

EXAMPLE 1

Methanol Only Production

A natural gas stream available at the process site at 35 atmospheres pressure is compressed to 120 atmospheres and then heated to 1050° F. Air is compressed to 120 atmospheres, heated to 900° F., and 320.55 MPH of this air is mixed and reacted with 102 MPH of the natural gas in the absence of a reforming catalyst to yield a reformed gas at a final temperature of 2150° F. comprising in MPH 93.35 CO, 158.9 hydrogen, 7.65 $CO_2$, 3 methane, 256.6 $N_2$ and 32.1 water.

The reformed gas is cooled to a temperature of 100° F. to condense about 31.8 MPH $H_2O$ which is separated to yield a synthesis gas having a pressure of 118 atmospheres. The synthesis gas is heated to about 450° F. and contacted with a methanol catalyst to produce 40 MPH methanol. The so reacted gas is then cooled to a temperature of 100° F. which condenses 39 MPH methanol and 0.3 MPH $H_2$ which are separated. The balance of the gas stream, now at a pressure of 114.1 atmospheres, is reheated to about 450° F. and passed into contact with a methanol catalyst then again cooled to 100° F. whereupon 14.7 MPH methanol and 0.2 MPH $H_2O$ condense and are separated. The gas stream balance is then reheated to 450° F. and again contacted with a methanol catalyst, then cooled to 100° F. and 7.4 MPH methanol and 0.1 MPH water condense and are separated.

The net methanol recovery is 61.1 MPH methanol with 0.4 MPH water. Conversion efficiency of input hydrocarbon carbon content to methanol is 60.5%.

The final gas balance has a pressure of 108.7 atmospheres and comprises in MPH 256.2 nitrogen, 31.65 CO, 34.9 $H_2$, 7.45 $CO_2$, 3 methane and 0.9 methanol. This final gas balance, or bleed gas, has a BTU value of 5,315,811 lower heating value. Scaling the above example up to a case of 30,000,000 scfd of natural gas, which calls for multiplication by a factor of 32,335, allows a total possible generation of 22,037 brake horsepower by the gas turbine. The energy required to compress the natural gas and air stream to the final pressure required for adiabatic reaction to provide a reformed gas is then respectively 2,417 and 15,284 brake horsepower. A net excess of energy available in the bleed gas of 4,336 brake horsepower is available for other uses, such as operation of an electrical generator.

EXAMPLE 2

Conversion to Methanol and Gasoline

A natural gas stream available at the process site at 35 atmospheres is compressed to 55 atmospheres and heated to 1050° F. Air is compressed to the same pressure and heated to 900° F. The so compressed and heated natural gas and air streams are combined at 102 MPH natural gas and 32.2 MPH air and reacted over a reforming catalyst to produce a reformed gas having a final temperature of 2100° F. and a pressure of 54.5 atmospheres, comprising, in MPH 94.9 CO, 163.1 $H_2$, 7.6 $CO_2$, 1.5 methane, 256.7 $N_2$, and 30.9 water. The reformed gas is cooled to 100° F. to condense 30.3 MPH water which is separated to yield as the balance a synthesis gas at a pressure of 54 atmospheres.

The synthesis gas is heated to 450° F. and contacted with a methanol only catalyst to produce 21.4 MPH methanol. The so-reacted gas, now at a pressure of 51.7 atmospheres, is cooled to 100° F. to condense 18.8 MPH methanol and 0.2 MPH water for separation. The balance of the gas stream is reheated to 450° F. and again contacted with a methanol only catalyst to yield a product gas stream containing 13.8 MPH methanol. Upon cooling to 100° F., 11.3 MHP methanol and 0.2 MPH water condense and are separated. The gas stream balance, now at a pressure of 50.50 atmospheres, is heated to 450° F. and contacted with a catalyst composition which coproduces methanol and DME to yield a gas stream comprising in MPH 15.15 CO, 49.9 $H_2$, 23.05 $CO_2$, 1.75 $H_2O$, 1.5 $CH_4$, 256.7 $N_2$, 16.55 DME and 1.1 methanol. This gas stream, now at a pressure of 48.5, is heated to a temperature of from about 700° to about 750° F. and contacted with a molecular sieve catalyst of HZSM-5 type. The so-reacted gas is cooled to 100° F. to condense and separate normally liquid hydrocarbon components and water, then reheated to 450° F. and contacted with a methanol-DME catalyst, then heated to 700°-750° F. and contacted with a second bed of molecular sieve catalyst. Upon cooling to 100° F., a further quantity of normally liquid hydrocarbons and water condense and are separated.

The total recovery of hydrocarbon carbon as normally liquid hydrocarbons is 35.9 MPH as carbon. In the above process, total recovery of input hydrocarbon carbon as methanol and gasoline is 65.3%. Of this, 30.1 MPH methanol is recovered and 35.9 MPH of carbon as normally liquid hydrocarbon components are recovered. The final vent or bleed gas after the last recovery of normally liquid hydrocarbons comprises in MPH 9.5 CO, 40.1 $H_2$, 23.65 $CO_2$, 1.8 $H_2O$, 1.5 methane, 256.7 N, and 3 MPH carbon atoms in hydrocarbon form, mostly ethylene. This bleed gas has a low heating BTU value of about 6,667,730. Scaling the above example up to a case of 30,000,000 scfd of natural gas by multiplication by a factor of 32.3356x, allows for the generation of about 27,682.5 brake horsepower by the gas turbine. The total energy required for compression of the natural gas and air is 10,830 brake horsepower. A net excess of about 16,752.5 brake horsepower is available from the bleed gas for operation of other equipment items, such as an electrical generator.

EXAMPLE 3

Conversion of Crude Associated Natural Gas to Methanol and Gasoline

Natural gas produced in association with petroleum crude is typically available at the process site at about 1.2 atmospheres. Such stream of natural gas is compressed to 55 atmospheres and thereafter processed in a manner identical to that described in Example 2, accordingly conversion and product recovery efficiencies are as described in the Example. At a scale of 30,000,000 scfd natural gas, the energy required for compression of the stream of natural gas to 55 atmospheres is 8,820 brake horsepower and for air is 10,068. A net excess of about 8,793.5 brake horsepower is available from the bleed gas for operation of other equipment items, such as an electrical generator.

The invention has been described with reference to its preferred embodiments. In view of this description, one skilled in the art may appreciate changes and modifications which may be made that do not depart from the scope and spirit of the invention as described above and claimed hereafter.

We claim:

1. In a process which converts natural gas into normally liquid carbon containing compounds by converting such natural gas into a synthetic gas containing $H_2$ and CO, then reacting such synthesis gas to convert a portion of the $H_2$ and CO content to normally liquid hydrocarbons compounds which are removed to leave a residual gas stream containing unreacted $H_2$, CO, and natural gas components; the improvement pertaining to the method for first converting such natural gas into the required synthesis gas comprising the steps of:
    (a) introducing an oxygen and nitrogen containing gas mixture containing about 21 mole % oxygen and 78 mole % nitrogen into the inlet of the compressor unit of a gas turbine;
    (b) introducing the residual gas stream containing unreacted $H_2$, CO and natural gas components into the fuel inlet of the expander drive unit of the gas turbine as driving fuel for the gas turbine;
    (c) diverting a quantity of the oxygen and nitrogen containing gas mixture from the compressed gas outlet of the gas turbine into the inlet of a gas compressor which is driven by the gas turbine for compression to a final pressure of from about 400 to about 2000 psia;
    (d) introducing natural gas into the inlet of a gas compressor driven by the gas turbine for compression to a final pressure of from about 400 to about 2000 psia;
    (e) heating the finally compressed oxygen and nitrogen containing gas mixture to a temperature of from about 700° to about 1400° F.;
    (f) heating the compressed natural gas to a temperature of from about 800° to about 1400° F.;
    (g) combining the compressed and heated natural gas with a quantity of the compressed and heated oxygen and nitrogen containing gas mixture which upon adiabatic reaction with such natural gas yields a reformed gas stream having a temperature of from about 1800° to about 2500° F. wherein $H_2$ is present in a molar ratio with respect to CO of from about 1.5 to about 1.9 and CO is present in a molar ratio with respect to $CO_2$ of from about 10 to about 25;
    (h) cooling said reformed gas stream to condense water; and
    (i) separating condensed water from said cooled reformed gas stream to yield a synthesis gas stream.

2. The process of claim 1, further comprising the steps of:
    (j) heating said synthesis gas stream to a temperature of from about 435° to about 500° F.; and
    (k) passing said gas stream at from about 400 to about 2000 psia into contact with a catalyst composition which promotes reaction between $H_2$ and CO to produce a product gas stream containing a quantity of methoxy compounds selected from the group consisting of methanol and dimethyl ether, and a balance comprising $N_2$, $H_2O$, CO, $H_2$ $CO_2$ and unreacted natural gas components.

3. The process of claim 2, further comprising the steps of:
    (l) introducing the product gas stream while at a temperature of from about 600° to 850° F. into contact with a molecular sieve catalyst composition to convert the methoxy compound content thereof into normally liquid hydrocarbon compounds; and
    (m) recovering liquid hydrocarbon compounds from the so-reacted product gas stream to yield a residual gas stream.

4. The process of claim 3 wherein said synthesis gas stream from step (j) is passed at a pressure of from about 400 to about 2000 psia into contact with a catalyst composition which promotes reaction between $H_2$ and CO to form a first quantity of methanol and thereafter further comprising the steps of (j') cooling said gas stream to condense and remove methanol and water from the synthesis gas stream; (j") heating said synthesis gas stream balance to a temperature from about 435° to about 500° F. and (j''') passing the synthesis gas stream balance after methanol and water removal as the gas stream to step (k).

5. The process of claim 3 wherein the residual gas stream is further treated by the step of:
    (n) recycling a portion of said residual gas stream into combination with said product gas stream of step (k).

6. In a process which converts natural gas into normally liquid carbon containing compounds by converting such natural gas into a synthesis gas containing $H_2$ and CO, then reacting such synthetic gas to convert a portion of the $H_2$ and CO content to normally liquid hydrocarbons compounds which are removed to leave a residual gas stream containing unreacted $H_2$, CO, and natural gas components; the improvement pertaining to the method for first converting such natural gas into the required synthesis gas comprising the steps of:

(a) introducing an oxygen containing gas mixture which has at least 50 mol % nitrogen into the inlet of the compressor unit of a gas turbine;

(b) introducing the residual gas stream balance containing unreacted $H_2$, CO and natural gas components into the fuel inlet of the expander drive unit of the gas turbine as driving fuel for the gas turbine;

(c) diverting a quantity of the oxygen and nitrogen containing gas mixture from the compressed gas outlet of the gas turbine into the inlet of a gas compressor which is driven by the gas turbine for compression to a final pressure of from about 400 to about 2000 psia;

(d) heating the compressed oxygen and nitrogen containing gas mixture to a temperature of from about 700° to about 1400° F.;

(e) heating natural gas at a pressure of from about 400 to about 2000 psia to a temperature of from about 800° to about 1400° F.;

(f) combining the heated natural gas with a quantity of the heated oxygen and nitrogen containing gas mixture which upon adiabatic reaction with such natural gas yields a reformed gas stream having a temperature of from about 1800° to about 2500° F. wherein $H_2$ is present in a molar ratio with respect to CO of from about 1.5 to about 1.9 and CO is present in a molar ratio with respect to $CO_2$ of from about 10 to about 25;

(g) cooling said reformed gas stream to condense water; and (h) separating condensed water from said cooler reformed gas stream to yield a synthesis gas stream.

* * * * *